(12) United States Patent
Ridland et al.

(10) Patent No.: US 6,372,929 B1
(45) Date of Patent: Apr. 16, 2002

(54) ESTERIFICATION CATALYSTS

(75) Inventors: John Ridland, Durham; Iain Wesley Hepplewhite, Teesside, both of (GB)

(73) Assignee: ACMA Limited, Cheshire (GB)

( * ) Notice: Subject to any disclaimer, the term of this patent is extended or adjusted under 35 U.S.C. 154(b) by 0 days.

(21) Appl. No.: 09/568,206

(22) Filed: May 9, 2000

Related U.S. Application Data

(63) Continuation of application No. PCT/GB98/03448, filed on Nov. 16, 1998.

(30) Foreign Application Priority Data

Dec. 2, 1997 (GB) .............................................. 9725419

(51) Int. Cl.$^7$ .............................. C07F 7/00; C07F 9/30; B01J 31/00
(52) U.S. Cl. ........................ 556/24; 556/174; 556/182; 502/162
(58) Field of Search .......................... 556/24, 174, 182; 502/162

(56) References Cited

U.S. PATENT DOCUMENTS 4,087,402 A * 5/1978 Monte et al. ............. 260/42.14
5,453,479 A * 9/1995 Borman et al. ............. 528/279

* cited by examiner

*Primary Examiner*—Porfirio Nazario-Gonzalez
(74) *Attorney, Agent, or Firm*—Pillsbury Winthrop LLP

(57) ABSTRACT

An organometallic compound suitable for use as a catalyst for the preparation of an ester comprises the reaction product of an orthoester or condensed orthoester of titanium, zirconium or aluminum, an alcohol containing at least two hydroxyl groups, an organophosphorus compound containing at least one P—OH group and a base. A process for the preparation of an ester comprises carrying out an esterification reaction in the presence of the catalyst In a further embodiment the organometallic compound suitable for use as a catalyst in an esterification process comprises the reaction product of, in addition, a 2-hydroxy carboxylic acid.

14 Claims, No Drawings

ESTERIFICATION CATALYSTS

This is a continuation under 35 U.S.C. Section 120 of International application Serial No. PCT/GB98/03448 filed on Nov. 16, 1998 which application designates the US.

The invention concerns esterification catalysts and in particular esterification catalysts which comprise novel organotitanium, organozirconium or organoaluminium compounds.

Organotitanium compounds and, in particular, titanium alkoxides or orthoesters are known as catalysts for esterification processes. During the esterification, these compounds are frequently converted to insoluble compounds of titanium which result in a hazy product The presence of a haze is a particular disadvantage in polyesters which have a high viscosity and/or high melting point and are therefore difficult to filter. Furthermore, many organotitanium compounds which are effective catalysts in the manufacture of polyesters such as polyethylene terephthalate are known to produce unacceptable yellowing in the final polymer. Our co-pending application, published as GB 2 314 081 relates to an esterification process in which these problems are partially solved but there is still a need for a catalyst which induces little or no yellowing in a polyester produced using the catalyst.

It is an object of the present invention to provide an improved catalyst for process for preparing esters.

According to the invention, an organometallic compound suitable-for use as a catalyst for the preparation of an ester comprises the reaction product of an orthoester or condensed orthoester of titanium, zirconium or aluminium, an alcohol containing at least two hydroxyl groups, an organophosphorus compound containing at least one P—OH group and a base.

Also according to the invention, a process for the preparation of an ester comprises carrying out an esterification reaction in the presence of a catalyst comprising the reaction product of an orthoester or condensed orthoester of titanium, zirconium or aluminium, an alcohol containing at least two hydroxyl groups, an organophosphorus compound containing at least one P—OH group and a base.

In a further embodiment the organometallic compound suitable for use as a catalyst in an esterification process comprises the reaction product of an orthoester or condensed orthoester of titanium, zirconium or aluminium, an alcohol containing at least two hydroxyl groups, an organophosphorus compound containing at least one P—OH group, a base and a 2-hydroxy carboxylic acid.

The organometallic compound of the invention is the reaction product of a titanium, zirconium or aluminium orthoester or condensed orthoester, an alcohol containing at least two hydroxyl groups, an organophosphorus compound containing at least one P—OH group and a base. Preferably, the orthoester has the formula $M(OR)_4$ or $AJ(OR)_3$ where M is titanium or zirconium and R is an alkyl group. More preferably R contains 1 to 6 carbon atoms and particularly suitable orthoesters include tetraisopropoxy titanium, tetra-n-butoxy titanium, tetra-n-propoxy zirconium, tetra-n-butoxy zirconium and tetra-iso-butoxy aluminium.

The condensed orthoesters suitable for preparing the compounds of this invention are typically prepared by careful hydrolysis of titanium, zirconium or aluminium orthoesters. Titanium or zirconium condensed orthoesters are frequently represented by the formula

$$R^1O[M(OR^1)_2O]_nR^1$$

in which $R^1$ represents an alkyl group and M represents titanium or zirconium. Preferably, n is less than 20 and more preferably is less than 10. Preferably, $R^1$ contains 1 to 12 carbon atoms, more preferably, $R_1$ contains 1 to 6 carbon atoms and useful condensed orthoesters include the compounds known as polybutyl titanate, polyisopropyl titanate and polybutyl zirconate.

Preferably, the alcohol containing at least two hydroxyl groups is a dihydric alcohol and can be a 1,2-diol such as 1,2-ethanediol or 1,2-propanediol, a 1,3-diol such as 1,3-propanediol, a 1,4-diol such as 1,4-butanediol, a diol containing non-terninal hydroxyl groups such as 2-methyl-2, 4pentanediol or a dihydric alcohol containing a longer chain such as diethylene glycol or a polyethylene glycol. Preferred dihydric alcohols are 1,2-ethanediol and diethylene glycol. The organometallic compound can also be prepared from a polyhydric alcohol such as glycerol, trimethylolpropane or pentaerythritol.

Preferably, the organometallic compound useful as a catalyst is prepared by reacting a dihydric alcohol with an orthoester or condensed orthoester in a ratio of from 1 to 16 moles of dihydric alcohol to each mole of titanium, zirconium or aluminium. More preferably, the reaction product contains 2 to 12 moles of dihydric alcohol per mole of titanium, zirconium or aluminium and most preferably 4 to 8 moles dihydric alcohol per mole of titanium, zirconium or aluminium.

The organophosphorus compound which contains at least one P—OH group can be selected from a number of organophosphorus compounds including phosphates, pyrophosphates, phosphonates, phosphinates and phosphites.

Preferably, the organophosphorus compound is a substituted or unsubstituted alkyl phosphate, a substituted or unsubstituted aryl phosphate or a phosphate of an alkylaryl glycol ether or an alkyl glycol ether. Preferred compounds include monoalkyl acid phosphates and dialkyl acid phosphates and mixtures of these. Particularly convenient organophosphorus compounds are the compounds commercially available as alkyl acid phosphates and containing, principally, a mixture of mono- and di-alkyl phosphate esters. When an alkyl phosphate is used, the organic group preferably contains up to 20 carbon atoms, more preferably up to 8 carbon atoms and, most preferably, up to 6 carbon atoms. When alkylaryl or alkyl glycol ether phosphates are used the carbon chain length is preferably up to 18 carbon atoms and, more preferably, 6 to 12 carbon atoms. Particularly preferred organophosphorus compounds include butyl acid phosphate, polyethylene glycol phosphates and aryl polyethylene glycol phosphates.

The amount of organophosphorus compound present in the reaction product of the invention is usually in the range 0.1 to 4.0 mole of phosphorus to 1 mole of metal (titanium, zirconium or aluminium), preferably in the range 0.1 to 2.0 mole phosphorus to 1 mole metal and most preferably in the range 0.1 to 1.0 mole phosphorus to 1 mole metal.

A base is also used in preparing the reaction product of the invention. The base is generally an inorganic base and suitable bases include sodium hydroxide, potassium hydroxide and ammonium hydroxide, but organic bases such as tetrabutyl ammonium hydroxide or choline hydroxide [trimethyl-(2-hydroxyethyl)ammonium hydroxide] can also be used. Usually, the amount of base used is in the range 0.1 to 4.0 mole base per mole of metal (titanium, zirconium or aluminium). The preferred amount is in the range 0.1 to 2.0 mole base per mole of metal and, frequently, the amount of base present is in the range 0.1 to 1.0 mole base per mole of titanium, zirconium or aluminium.

When 2-hydroxy carboxylic acids are used to prepare the products of the invention, preferred acids used include lactic acid, citric acid, malic acid and tartaric acid. Some suitable acids are supplied as hydrates or as aqueous mixtures and can be used in this form. When a 2-hydroxy acid is present, the preferred molar ratio of acid to titanium, zirconium or aluminium in the reaction product is 0.5 to 4 moles per mole of titanium, zirconium or aluminium. More preferably the catalyst contains 1.0 to 3.5 moles of 2-hydroxy acid per mole of titanium, zirconium or aluminium.

The organometallic compound can be prepared by mixing the components (orthoester or condensed orthoester, alcohol containing at least two hydroxyl groups, organophosphorus compound and base) with removal, if desired, of any by-product, (e.g. isopropyl alcohol when the orthoester is tetraisopropoxytitanium), at any appropriate stage. In one preferred method the orthoester or condensed orthoester and a dihydric alcohol are mixed and, subsequently, a base is added, followed by the organophosphorus compound. When a 2-hydroxy carboxylic acid is also present in the reaction product, this is usually added to the orthoester or condensed orthoester before the organophosphorus compound is added. Alternatively, all or part of the 2-hydroxy carboxylic acid can be neutralised with the base and the resulting salt added to the other components of the reaction mixture, including, if desired, a further portion of the base.

The esterification reaction of the process of the invention can be any reaction by which an ester is produced. The reaction may be (i) a direct esterification in which a carboxylic acid or its anhydride and an alcohol react to form an ester or (ii) a transesterification (alcoholysis) in which a first alcohol reacts with a first ester to produce an ester of the first alcohol and a second alcohol produced by cleavage of the first ester or (iii) a transesterification reaction in which two esters are reacted to form two different esters by exchange of alkoxy radicals. Direct esterification or transesterification can be used in the production of polymeric esters and a preferred process of the invention comprises a polyesterification process. Many carboxylic acids and anhydrides can be used in direct esterification including saturated and unsaturated monocarboxylic acids and anhydrides of such acids such as stearic acid, isostearic acid, capric acid, caproic acid, palmitic acid, oleic acid, palmitoleic acid, triacontanoic acid, benzoic acid, methyl benzoic acid, salicylic acid and rosin acids such as abietic acid, dicarboxylic acids such as phthalic acid, isophthalic acid, terephthalic acid, sebacic acid, adipic acid, azelaic acid, succinic acid, fumaric acid, maleic acid, naphthalene dicarboxylic acid and pamoic acid and anhydrides of these acids and polycarboxylic acids such as trimellitic acid, citric acid, trimesic acid, pyromellitic acid and anhydrides of these acids. Alcohols frequently used for direct esterification include aliphatic straight chain and branched monohydric alcohols such as butyl, pentyl, hexyl, octyl and stearyl alcohols, dihydric alcohols such as 1,2-ethanediol, 1,3-propanediol, 1,4-butanediol and 1,6-hexanediol and polyhydric alcohols such as glycerol and pentaerythritol. A preferred process of the invention comprises reacting 2-ethylhexanol with phthalic anhydride to form bis(2-ethylhexyl)phthalate.

The esters employed in an alcoholysis reaction are generally the lower homologues such as methyl, ethyl and propyl esters since, during the esterification reaction, it is usual to eliminate the displaced alcohol by distillation. These lower homologue esters of the acids suitable for direct esterification are suitable for use in the transesterification process according to the invention. Frequently (meth) acrylate esters of longer chain alcohols are produced by alcoholysis of esters such as methyl acrylate, methyl methacrylate, ethyl acrylate and ethyl methacrylate. Typical alcohols used in alcoholysis reactions include butyl, hexyl, n-octyl and 2-ethyl hexyl alcohols and substituted alcohols such as dimethylaminoethanol.

When the esterification reaction is a transesterification between two esters, generally the esters will be selected so as to produce a volatile product ester which can be removed by distillation.

As mentioned hereinbefore, polymeric esters can be produced by processes involving direct esterfication or transesterification and a particularly preferred embodiment of the esterification process of the invention is a polyesterification reaction in the presence of the catalyst described hereinbefore. In a polyesterification reaction polybasic acids or esters of polybasic acids are usually reacted with polyhydric alcohols to produce a polymeric ester. Linear polyesters are often produced from dibasic acids such as those mentioned hereinbefore or esters of said dibasic acids and dihydric alcohols. Preferred polyesterification reactions according to the invention include the reaction of terephthalic acid or dimethyl terephthalate with 1,2-ethanediol (ethylene glycol) to produce polyethylene terephthalate or with 1,4-butanediol (butylene glycol) to produce polybutylene terephthalate or reaction of naphthalene dicarboxylic acid with 1,2-ethanediol to produce polyethylene naphthalenate. Other glycols such as 1,3-propanediol, 1,6-hexanediol and polyhydric alcohols such as glycerol, trimethylolpropane and pentaerythritol are also suitable for preparing polyesters.

The esterification reaction of the invention can be carried out using any appropriate, known technique for an esterification reaction.

A typical process for the preparation of polyethylene terephthalate comprises two stages. In the first stage terephthalic acid or dimethyl terephthalate is reacted with 1,2-ethanediol to form a prepolymer and the by-product water or methanol is removed. The prepolyrner is subsequently heated in a second stage to remove 1,2-ethanediot and form a long chain polymer. Either or both these stages may comprise an esterification process according to this invention.

In direct esterification the acid or anhydride and an excess of alcohol are typically heated, if necessary in a solvent, in the presence of the catalyst. Water is a by-product of the reaction and this is removed, as an azeotrope with a boiling mixture of solvent and/or alcohol. Generally, the solvent and/or alcohol mixture which is condensed is immiscible with water which is therefore separated before solvent and/or alcohol are returned to the reaction vessel. When reaction is complete the excess alcohol and, when used, solvent are evaporated. In view of the fact that the catalysts of the invention do not normally form insoluble species, it is not generally necessary to remove them from the reaction mixture, as is frequently necessary with conventional catalysts. A typical direct esterification reaction is the preparation of bis(2-ethylhexyl) phthalate which is prepared by mixing phthalic anhydride and 2-ethyl hexanol. An initial reaction to form a monoester is fast but the subsequent conversion of the monoester to diester is carried out by refluxing in the presence of the catalyst at a temperature of 180–200° C. until all the water has been removed. Subsequently the excess alcohol is removed.

In an alcoholysis reaction, the ester, first alcohol and catalyst are mixed and, generally, the product alcohol (second alcohol) is removed by distillation often as an azeotrope with the ester. Frequently it is necessary to fractionate the vapour mixture produced from the alcoholysis in order to ensure that the second alcohol is separated effectively without significant loss of product ester or first alcohol. The conditions under which alcoholysis reactions are carried out depend principally upon the components of the reaction and generally components are heated to the boiling point of the mixture used.

A preferred process of the invention is the preparation of polyethylene terephthalate. A typical batch production of polyethylene terephthalate is carried out by charging terephthalic acid and ethylene glycol to a reactor along with catalyst if desired and heating the contents to 260–270° C. under a pressure of about 0.3 MPa. Reaction commences as the acid dissolves at about 230° C. and water is removed. The product is transferred to a second autoclave reactor and catalyst is added, if needed. The reactor is heated to 285–310° C. under an eventual vacuum of 100 Pa to remove ethylene glycol by-product. The molten product ester is discharged from the reactor, cooled and chipped. The chipped polyester may be then subjected to solid state polymerisation, if appropriate.

The amount of catalyst used in the esterification process of the invention generally depends upon the titanium, zirconium or aluminium content, expressed as Ti, Zr or Al, of the catalyst Usually the amount is from 30 to 1000 parts per million (ppm) of metal on weight of product ester for direct or transesterification reactions. Preferably, the amount is from 30 to 450 ppm of metal on weight of product ester and more preferably 50 to 450 ppm of metal on weight of product ester. in polyesterification reactions the amount used is generally expressed as a proportion of the weight of product polyester and is usually from 5 to 500 ppm expressed as Ti, Zr or Al based on product polyester. Preferably the amount is from 5 to 100 ppm expressed as Ti, Zr or Al based on product polyester.

The products of this invention have been shown to be effective catalysts for producing esters and polyesters at an economical rate without leading to haze in the final product and with a reduced amount of yellowing of polyesters in comparison to known catalysts. They have also been shown to be stable against precipitation from polyester products when aqueous base or phosphoric acid is added to such products.

The invention is illustrated by the following examples.

Preparation of Compounds for use as Catalysts

EXAMPLE 1

Ethylene glycol (496.0 g, 8.00 moles) was added from a dropping funnel to stirred titanium n-butoxide (340 g, 1.00 mole) in a 1 liter fishbowl flask fitted with stirrer, condenser and thermometer. An aqueous solution of sodium hydroxide, containing 32% NaOH by weight, (125 g, 1.00 mole) was added to the reaction flask slowly with mixing to yield a clear pale yellow liquid. To this liquid was then added a polyethylene glycol phosphate having a carbon chain length of 12 carbon atoms and available commercially under the trade name Knapsack 194, (215.8 g, 0.55 mole of phosphorus) and the resulting mixture was stirred for 1 hour to produce a pale yellow liquid with a Ti content of 4.07% by weight.

EXAMPLE 2

The method of Example 1 was repeated with the difference that 0.28 mole based on phosphorus (107.9 g) Knapsack 194 was added. The product was a pale yellow liquid with a Ti content of 4.49% by weight.

EXAMPLE 3

The method of Example 1 was repeated but 0.50 mole, based on phosphorus (91.0 g) commercial butyl acid phosphate (mixture of mono and di-butyl acid phosphates) was used in place of the Knapsack 194. The product was a pale yellow liquid with a Ti content of 4.56% by weight.

EXAMPLE 4

The method of Example 3 was repeated except that the amount of butyl acid phosphate used was 1.00 mole based on phosphorus (182.0 g). The product was a pale yellow liquid with a Ti content of 4.20% by weight.

EXAMPLE 5

The method of Example 1 was repeated but 0.64 mole based on phosphorus (431.6g) of an aryl polyethylene glycol phosphate, sold commercially under the trade name Knapsack 123 was used in place of the Knapsack 194. The product was a pale yellow liquid with a Ti content of 3.45% by weight.

EXAMPLE 6

The method of Example 5 was repeated except that the amount of Knapsack 123 used was 0.32 mole based on phosphorus (215.8 g). The product was a pale yellow liquid with a Ti content of 4.08% by weight.

EXAMPLE 7

Ethylene glycol (248.0 g, 4.0 moles) was added dropwise to stirred titanium isopropoxide (142 g, 0.5 moles) in a 1 liter fishbowl flask fitted with a stirrer, thermometer and condenser. Aqueous potassium lactate (60% by weight, 213.5 g, 1.0 mole) was added from a dropping funnel to the clear solution which was then heated to 65° C. under vacuum and volatile solvents were removed to yield a clear, pale yellow liquid. A portion (82.19 g, 0.1 mole Ti) was weighed into a 250 ml conical flask and commercial butyl acid phosphate (9.1 g, 0.05 moles based on phosphorus) was added from a dropping funnel with stirring. The final product was a clear, pale yellow liquid (Ti content 5.26% by weight).

EXAMPLE 8

Ethylene glycol (49.6 g, 0.8 moles) was added by dropping funnel to stirred titanium n-butoxide (34.0 g, 0.1 mole) in a 250 ml conical flask. An aqueous solution of sodium hydroxide containing 32% NaOH by weight (12.5 g, 0.1 mole) was added followed by a polyethylene glycol phosphate having a carbon chain length of 12 and available commercially under the trade name Knapsack 122 (32.3 g, 0.05 moles based on phosphorus). The resulting product was a white solid having a Ti content of 3.74% by weight

EXAMPLE 9

Ethylene glycol (49.6 g, 0.8 mole) was added by dropping funnel to stirred titanium n-butoxide (34.0 g, 0.1 mole) in a 250 ml conical flask. An aqueous solution of sodium hydroxide containing 32% NaOH by weight (12.5 g, 0.1 mole) was added followed by dibutyl phosphate (10.5 g, 0.05 mole). The resulting product was a hazy liquid having a measured Ti content of 4.56% by weight.

EXAMPLE 10

Monoethylene glycol (49.6 g, 0.8 mole) was added by dropping funnel to stirred condensed titanium alkoxide known as polybutyl titanate (Tilcom® PBT) (Ti content 20.0% by wt) (24.2 g, 0.10 moles Ti) in a 250 ml conical flask. An aqueous solution of sodium hydroxide containing 32% NaOH by weight (12.5 g, 0.1 mole) was added followed by a commercial butyl phosphate (9.1 g, 0.05 mole based on phosphorus). The resulting product was a white solid having a Ti content of 5.03% by weight.

EXAMPLE 11

Diethylene glycol (848 g, 8.0 moles) was added by dropping funnel to stirred zirconium n-propoxide (Tilcom® NPZ) (445 g, 1.0 mole Zr) in a 2 liter-flask. A portion of this solution (129.3 g, 0.1 moles Zr) was weighed into a 250 ml conical flask and an aqueous solution containing 45% choline hydroxide by weight (13.45 g, 0.05 moles) was added followed by a commercial butyl phosphate (9.1 g, 005 moles based on phosphorus). The resulting product was a clear yellow solution having a Zr content of 6.01% by weight.

EXAMPLE 12

Diethylene glycol (84.8 g, 0.8 mole) was added by dropping funnel to stirred aluminium sec-butoxide (24.6 g, 0.1 mole) in a 250 ml conical flask. An aqueous solution of sodium hydroxide containing 32% NaOH by weight (12.5 g, 0.1 mole) was added followed by a commercial butyl phosphate (9.1 g, 0.05 mole based on phosphorus). The resulting product was a clear solid gel having an Al content of 2.06% by weight

EXAMPLE 13

Ethylene glycol (24.8 g, 0.4 mole) was added by dropping funnel to stirred titanium n-butoxide (34.0 g, 0.1 mole) in a 250 ml conical flask. An aqueous solution containing 45% by weight of choline hydroxide (26.93 g, 0.1 mole) was added followed by a cormmercial butyl phosphate (18.2 g, 0.1 mole based on phosphorus). The resulting product was a clear pale yellow liquid having a Ti content of 4.62% by weight.

EXAMPLE 14

Ethylene glycol (99.2 g, 1.6 mole) was added by dropping funnel to stirred titanium n-butoxide (68.1 g, 0.2 mole) in a 250 ml conical flask. An aqueous solution of sodium hydroxide containing 32% by weight NaOH (25.0 g, 0.2 mole) was added followed by commercial butyl phosphate (18.2 g, 0.1 mole). The resulting clear liquid product was transferred to a 500 ml rotary evaporator flask and solvents were removed under vacuum at 95° C. to yield a hazy liquid having a Ti content of 10.54% by weight.

Esterification

EXAMPLE 15

The products of Examples 1, 3, 5 and 7 were tested at a concentration of 170 ppm Ti as catalysts for the preparation of bis(2-ethylhexyl phthalate). Titanium tetra-isopropoxide [Ti(OPr$^i$)$_4$] was used as a comparative catalyst The apparatus was a 1-liter, 4-necked round-bottomed flask fitted with a thermometer, rubber seal, a tube dipping below the surface of the reactants and a Dean and Stark apparatus. The equipment was operated under reduced pressure using an oil vacuum pump connected to two water condensers fitted above the Dean and Stark apparatus. The dip tube in the flask was connected to a supply of oxygen-free nitrogen. This provided a nitrogen bleed to aid the removal of water during the reaction.

1.0 mole (148 g) phthalic anhydride was added to 2.42 moles (315 g) 2-ethylhexanol. The mixture was heated to dissolve the phthalic anhydride and the nitrogen flow started.

A weighed amount of catalyst was added to the reaction flask in a porcelain boat before heating the mixture, except for Ti(OPr$^i$)$_4$ which was added as a solution in 2-ethylhexanol via the rubber seal with a syringe, below the surface of the reactants. The reaction mixture was heated to and maintained at a vigorous reflux at 200° C. by suitable adjustment of the heating rate and vacuum. The water produced was removed substantially as quickly as it was formed and collected in the Dean and Stark apparatus.

The progress of the reaction was followed by withdrawing samples at intervals by means of a syringe fitted with a 30 cm needle inserted through the rubber seal. Each sample was added to a known weight (approximately 100 g) of cold alcohol to quench the reaction, weighed and titrated against standard potassium hydroxide solution in ethanol using bromophenol blue as indicator. The results were used to calculate the amount of unreacted half-ester present.

The reaction was continued for a total of 160 minutes.

The results are given in Table 1 below:

TABLE 1

| Catalyst | Product Colour[1] | Product Clarity | % Conversion |
| --- | --- | --- | --- |
| Ti(OPr$^i$)$_4$ | 85 | Hazy | 99.95 |
| Example 1 | 70 | Clear | 98.59 |
| Example 3 | 60 | Clear | 96.43 |
| Example 5 | 70 | Clear | 97.64 |
| Example 7 | 80 | Clear | 93.54 |

[1]Hazen units. Colour of final reaction mixture.

EXAMPLE 16

The products of Examples 3, 5 and 8 to 14 were tested at a concentration of 164 ppm Ti or A or 340 ppm Zr based on reactants as catalysts for the preparation of monoethyleneglycol benzoate. Titanium isopropoxide [Ti(OPr$^i$)$_4$] and antimony oxide were used as comparative examples.

The apparatus was a 1-liter, 4-necked round bottom flask fitted with thermometer, rubber seal, dip tube below the surface of reactants and Dean and Stark apparatus. A glass column (30 cm) containing glass beads was attached between the reaction flask and Dean and Stark apparatus. The equipment was operated under vacuum using an oil vacuum pump connected to a water condenser above the Dean and Stark apparatus. The dip tube was connected to a supply of oxygen-free nitrogen and provided a nitrogen bleed to aid the removal of water during the reaction. 0.5 mole (61.06 g) benzoic acid was added to 10 moles (620 g) monoethylene glycol. The excess of glycol was used to prevent benzoic acid sublimation and to minimise polycondensation reactions. The catalysts were added as solutions or suspensions in the monoethyleneglycol to ensure good dispersion. The mixture was heated to dissolve the benzoic acid and the nitrogen flow started. The temperature was raised to 180° C. and after 5 minutes a slight vacuum was applied and the temperature raised to 200° C. Distillation of the water/monoethylene glycol commenced at about 150° C. and the reactions were maintained at a vigorous reflux at 190 to 193° C. by suitable adjustment of heating rate and vacuum. The water produced was removed with monoethyleneglycol and collected via the Dean and Stark apparatus.

Progress of the reaction was followed by withdrawing samples at intervals by means of a syringe fitted with a 30 cm needle inserted through the rubber seal Each sample was added to a known weight (approximately 100 g) of cold alcohol to quench the reaction, weighed and titrated against standard potassium hydroxide solution in ethanol using bromophenol blue as indicator. The results of acid value (AV) were used to calculate the percentage conversion to benzoate ester. The reactions were each monitored for a total of 180 minutes. The results are given in Table 2 below.

TABLE 2

| Catalyst | % Conversion | | | | Ester Colour |
|---|---|---|---|---|---|
| | 90 min. | 120 min. | 150 min. | 180 min. | |
| Sb oxide* | 46.09 | 53.05 | 61.05 | 66.16 | pale yellow |
| Ti(OPr$^i$)$_4$ | 70.63 | 81.84 | 99.67 | 99.39 | colourless |
| Example 8 | 92.83 | 98.59 | 99.39 | 99.53 | colourless |
| Example 9 | 96.60 | 99.27 | 99.62 | 99.61 | colourless |
| Example 10 | 94.91 | 97.42 | 98.03 | 98.52 | colourless |
| Example 11 | 45.93 | 50.40 | 50.97 | 54.60 | white/cloudy |
| Example 12 | 32.09 | 38.50 | 44.50 | 50.44 | white/cloudy |
| Example 13 | 97.61 | 98.43 | 99.76 | 99.87 | colourless |
| Example 14 | 95.75 | 98.27 | 99.48 | 99.66 | colourless |
| Example 5 | 97.23 | 97.54 | 98.04 | 99.60 | colourless |
| Example 3 | 98.56 | 99.01 | 99.10 | 99.78 | colourless |

*Amspec Select Antimony Oxide (3% wt/wt monoethylene glycol) at 164 ppm Sb.

After the reaction flask had cooled, a sample was removed for gas chromatographic (GC) analysis. It was found that different catalysts produced varying proportions of the products. The products formed were ethyleneglycol monobenzoate (EGMB), ethyleneglycol dibenzoate (EGDB), diethyleneglycol (DEG), diethyleneglycol monobenzoate (DEGMB) and fethylene glycol dibenzoate (DEGDB). The proportions (by area % from GC) are reported in Table 3.

TABLE 3

| Catalyst | EGMB | EGDB | DEG | DEGMB | DEGDB |
|---|---|---|---|---|---|
| Sb oxide* | 6.67 | 0.72 | 0.48 | 2.75 | — |
| Ti(OPr$^i$)$_4$ | 1.71 | 17.26 | 0.46 | 0.47 | 3.95 |
| Example 8 | 1.93 | 12.89 | ca 0.04 | 0.08 | 0.71 |
| Example 9 | 1.94 | 12.88 | ca 0.04 | 0.24 | 0.48 |
| Example 10 | 1.98 | 14.58 | ca 0.08 | 0.26 | 0.30 |
| Example 11 | 1.38 | 3.93 | 0.53 | 0.45 | 2.36 |
| Example 12# | 0.91 | 4.01 | 0.70 | 0.41 | 1.39 |
| Example 13# | 2.16 | 15.62 | 0.15 | 0.27 | 0.77 |
| Example 14 | 1.79 | 19.87 | ca 0.07 | 0.30 | 0.91 |
| Example 5 | 3.02 | 25.60 | 0.28 | 0.24 | 1.28 |
| Example 3 | 2.61 | 19.10 | 0.1 | 0.21 | 0.91 |

*Amspec Select Antimony Oxide (3% wt/wt monoethylene glycol) at 164 ppm Sb.
Analysis of supernatant liquor.

The results demonstrate that the catalysts of the invention are effective for the esterification reaction of benzoate esters and produce products with lower levels of DEG by-product than antimony oxide or conventional titanium catalysts.

EXAMPLE 17

A polycondensation reaction was carried out in a mechanically-stirred 300 ml glass vessel fitted with side arm and cold trap for collection of monoethyleneglycol. A thermostatically controlled ceramic heating element was used to provide heat and an oil vacuum pump was connected to the cold trap. A nitrogen blanket was provided via a connection to the cold trap.

Polyethylene terephthalate was prepared from (hydroxyethyl)terephthalate polymer precursors supplied by ICI Polyesters. Two samples were used; sample A was a short chain polymer containing approximately 4 ethylene terephthalate repeating units whilst sample B was technically pure bis(hydroxyethyl)terephthalate. Sample A also contained approximately 5 mol % acid end groups.

100 g of (hydroxy)terephthalate polymer precursor was placed in the reaction flask under a nitrogen flow, followed by a dilute solution of catalyst (Ti added at 30 ppm) in monoethyleneglycol. This was heated with stirring to 250° C. for 20–25 minutes at which point a stabiliser (phosphoric acid, 100 ppm) and cobalt acetate tetrahydrate (250 ppm) were added, again as solutions in monoethyleneglycol. The nitrogen flow was stopped and vacuum applied steadily to 100 Pa. After 20–25 minutes the temperature was increased steadily from 250° C. to 290° C. The power consumption of the electrical stirrer increased with the viscosity of the polymer and the stirrer revolutions dropped. The revolutions were monitored until a predetermined value for the peripheral speed of the agitator tip (15 km/h) was reached at which point the vacuum was broken with nitrogen and the molten polymer discharged and quenched into cold water. It was then dried for 10–14 hours at 50° C. in a vacuum oven.

The colour of the polymer was measured using a Colorgard System 2000 Colorimeter. Common models to use for colour expression are the Hunter Lh, ah and bh or Cielab L*, a* and b* scales where the b-value in both describe yellowness. The yellowness of the polymer increases with b-value.

The polymer molecular weights were measured by Gel Permeation Chromatography (GPC).

The results are given in Table 4.

TABLE 4

| Catalyst | Monomer Sample | Reaction Time (Minutes) | Colour (b* value) | Colour (bh value) | Molecular Weight (Mn) |
|---|---|---|---|---|---|
| Sb oxide# | A | 195 | 6 | 5.32 | 19,330 |
| Ti(OPr$^i$)$_4$ | A | 110 | 6.7 | 5.37 | 16,290 |
| Example 5 | A | 140 | 3.39 | 2.78 | 11,480 |
| Example 3 | A | 145 | 3.34 | 2.57 | 14,130 |
| Sb oxide# | B | 135 | 0.71 | 0.56 | 19,550 |
| Ti(OPr$^i$)$_4$ | B | 115 | 9.06 | 6.67 | 15,190 |
| Example 5 | B | 80 | 5.93 | 4.63 | 12,770 |
| Example 3 | B | 100 | 4.05 | 2.9 | 15,420 |
| Example 10 | B | 100 | 8.65 | 6.30 | NA |
| Example 13 | B | 95 | 4.47 | 3.56 | NA |

Antimony oxide Catalyst Grade from SICA added at 250 ppm Sb.
NA - not available.

These results indicate that the catalysts of the invention are active for the preparation of polyethylene terephthatate and are capable of producing polymer with lower yellowness values than conventional titanium-based catalysts.

EXAMPLE 18

It has been postulated that one mechanism causing discolouration when titanium catalysts are used to prepare polyethylene terephthalate is interaction of the catalyst with a thermal decomposition product of polyethylene terephthalate. Catalysts of Examples 1 to 7 were assessed by mixing with one such decomposition product, diethyidihydroxy terephthalate (DEDHT) in toluene. The standard catalyst, titanium tetra-isopropoxide [Ti(OPr$^i$)$_4$] was used for comparison and was added to 0.4 g DEDHT in 10 ml toluene. The catalysts of Examples 1 to 7 were added to DEDHT/toluene solution of a similar concentration in an amount sufficient to produce the same Ti concentration in the mixture and the colour of each of the mixtures was determined using a LICO 200 spectrophotometer in 11 ml glass cuvettes The results are given in Table 5.

TABLE 5

| Catalyst | Colour (Gardner units) |
| --- | --- |
| None | 6 |
| Ti(OPr$^i$)$_4$ | 11.9 |
| Example 1 | 6 |
| Example 2 | 8.5 |
| Example 3 | 5.5 |
| Example 4 | 5.5 |
| Example 5 | 5.5 |
| Example 6 | 8.5 |
| Example 7 | 7 |

What is claimed is:

1. An organometallic compound suitable for use as a catalyst for the preparation of an ester comprising the reaction product of an orthoester or condensed orthoester of titanium, zirconium or aluminium, an alcohol containing at least two hydroxyl groups, an organophosphorus compound containing at least one P—OH group and a base.

2. An organometallic compound according to claim 1 comprising the reaction product of an orthoester or condensed orthoester of titanium, zirconium or aluminium, an alcohol containing at least two hydroxyl groups, an organophosphorus compound containing at least one P—OH group, a base and a 2-hydroxy carboxylic acid.

3. An organometallic compound according to claim 2 characterised in that the 2-hydroxy acid is lactic acid, citric acid, malic acid or tartaric acid.

4. An organometallic compound according to claim 1 characterised in that the orthoester has the formula M(OR)$_4$ or Al(OR)$_3$ where M is titanium or zirconium and R is an alkyl group containing from 1 to 6 carbon atoms.

5. An organometallic compound according to claim 1 characterised in that the condensed orthoester has a structure which can be represented by the formula, R$^1$O[M(OR$^1$)$_2$O]$_n$R$^1$ where M is titanium or zirconium, R$^1$ is an alkyl group containing 1 to 6 carbon atoms and n is less than 20.

6. An organometallic compound according to claim 1 characterised in that the alcohol containing at least two hydroxyl groups is 1,2-ethanediol, 1,2-propanediol, 1,3-propanediol, 1,4-butanediol, 2-methyl-2,4-pentanediol, diethylene glycol, polyethylene glycol, glycerol, trimethylol-propane or pentaerythritol.

7. An organometallic compound according to claim 1 and comprising the reaction product of an orthoester or condensed orthoester of titanium, zirconium or aluminium, an alcohol containing at least two hydroxyl groups, an organophosphorus compound containing at least one P—OH group and a base characterised in that said alcohol is a dihydric alcohol and wherein the amount of dihydric alcohol is from 1 to 16 moles of dihydric alcohol to each mole of titanium, zirconium or aluminium.

8. An organometallic compound according to claim 1 characterised in that the organophosphorus compound is a phosphate, a pyrophosphate, a phosphonate, a phosphinate or a phosphite.

9. An organometallic compound according to claim 1 characterised in that the organophosphorus compound is a substituted or unsubstituted alkyl phosphate, a substituted or unsubstituted aryl phosphate or a phosphate of an alkylaryl glycol ether or an alkyl glycol ether.

10. An organometallic compound according to claim 1 characterised in that the organophosphorus compound is an alkyl phosphate in which the organic group contains up to 20 carbon atoms.

11. An organometallic compound according to claim 1 characterised in that the organophosphorus compound is a phosphate of an alkylaryl glycol ether or an alkyl glycol ether having a carbon chain length up to 18 carbon atoms.

12. An organometallic compound according to claim 1 characterised in that the organophosphorus compound is present in an amount in the range 0.1 to 4.0 mole of phosphorus to 1 mole of titanium, zirconium or aluminium.

13. An organometallic compound according to claim 1 characterised in that the base is present in an amount in the range 0.1 to 4.0 mole of base to 1 mole of titanium, zirconium or aluminium.

14. An organometallic compound according to claim 2 characterised in that the 2-hydroxy acid is present in an amount in the range 0.5 to 4 mole acid to 1 mole of titanium, zirconium or aluminium.

* * * * *